United States Patent [19]

Nelson et al.

[11] Patent Number: 5,326,585

[45] Date of Patent: Jul. 5, 1994

[54] METHOD AND COMPOSITIONS FOR MANUFACTURE OF CHEMICAL SENSORS

[75] Inventors: Alan M. Nelson; Carmen L. Soikowski, both of San Diego, Calif.

[73] Assignee: Puritan-Bennett Corporation, Carlsbad, Calif.

[21] Appl. No.: 108,108

[22] Filed: Aug. 17, 1993

Related U.S. Application Data

[63] Continuation of Ser. No. 874,031, Apr. 27, 1992, Pat. No. 5,262,192.

[51] Int. Cl.$^5$ ............................ G02B 6/22; B05D 5/06
[52] U.S. Cl. .................................. 427/163; 422/82.05; 385/128; 385/145
[58] Field of Search ................ 427/2, 163, 407.2, 379, 427/293; 356/39; 436/68, 167, 172; 65/3, 11; 385/128, 145; 422/82, 82.05, 82.06, 82.07, 82.08, 82.09, 58

[56] References Cited

U.S. PATENT DOCUMENTS

| | | | |
|---|---|---|---|
| 4,425,375 | 1/1984 | Abramson | 427/513 |
| 4,446,293 | 5/1984 | König et al. | 528/45 |
| 4,557,900 | 12/1985 | Heitzmann | 422/55 |
| 4,671,937 | 6/1987 | Katsuyama et al. | 422/56 |
| 4,712,865 | 12/1987 | Hsu et al. | 350/96.29 |
| 4,714,770 | 12/1987 | Hsu et al. | 556/419 |
| 4,746,751 | 5/1988 | Oviatt, Jr. et al. | 556/456 |
| 4,752,115 | 6/1988 | Murray, Jr. et al. | 350/96.29 |
| 4,798,738 | 1/1989 | Yafuso et al. | 427/2 |
| 4,824,789 | 4/1989 | Yafuso et al. | 436/68 |
| 4,842,783 | 6/1989 | Blaylock | 264/1.4 |
| 4,849,172 | 7/1989 | Yafuso et al. | 422/55 |
| 4,861,727 | 8/1989 | Hauenstein et al. | 436/136 |
| 4,867,919 | 9/1989 | Yafuso et al. | 264/1.5 |
| 4,886,338 | 12/1989 | Yafuso et al. | 350/96.29 |
| 4,925,268 | 5/1990 | Iyer et al. | 350/96.29 |
| 5,056,520 | 10/1991 | Tomisaka et al. | 128/634 |
| 5,132,057 | 7/1992 | Tomisaka et al. | 264/1.4 |
| 5,152,287 | 10/1992 | Kane | 128/634 |
| 5,236,667 | 8/1993 | Puschett et al. | 422/82.11 |
| 5,262,192 | 11/1993 | Nelson et al. | 427/2 |
| 5,266,271 | 11/1993 | Bankert et al. | 422/82.07 |

FOREIGN PATENT DOCUMENTS 0363993 4/1990 European Pat. Off. .
WO88/05533A 7/1988 PCT Int'l Appl. .

OTHER PUBLICATIONS

Munkholm et al., *A Fiber-Optic Sensor for $CO_2$ Measurement*, 1988, vol. 35, pp. 109–112.

Munkholm et al., *Polymer Modification of Fiber Optic Chemical Sensors as a Method of Enhancing Fluorescence Signal for pH Measurement*, Anal Chem. 58, 1427–1430, 1986 (Feb.).

*Primary Examiner*—Shrive Beck
*Assistant Examiner*—Diana L. Dudash
*Attorney, Agent, or Firm*—Fulwider Patton Lee & Utecht

[57] ABSTRACT

The method for making an optical fiber microsensor involves applying an uncured analyte sensing matrix to an optical fiber and crosslinking the sensing matrix in situ on the optical fiber to yield an ion permeable microsensor which can be used intravascularly to monitor pH, or partial pressures of oxygen or carbon dioxide in blood. The liquid form of the sensing matrix contains a crosslinking agent and a crosslinking inhibitor which can be removed by exposure to elevated temperatures to allow the sensing matrix to crosslink and cure as desired, in situ, on the surface of the optical fiber. A liquid crosslinking overcoat layer containing a crosslinking agent and a crosslinking inhibitor which can be removed by exposure to heat can also be applied over the cured sensing matrix.

30 Claims, No Drawings ical and chemical bonding between the sensing matrix and the optical fiber.

METHOD AND COMPOSITIONS FOR MANUFACTURE OF CHEMICAL SENSORS

This is a continuation of application Ser. No. 07/874,031, filed Apr. 27, 1992, now U.S. Pat. No. 5,262,192.

BACKGROUND OF THE INVENTION

1. Field of the Invention

This invention is generally directed to sensors for chemical and biomedical analysis of constituents of a fluid or gaseous mixture, and more specifically concerns methods and compositions for manufacturing optical fiber sensors for measuring blood constituents such as oxygen, carbon dioxide, and pH.

2. Description of Related Art

Optical fiber sensors for measuring pH, oxygen and carbon dioxide have been developed for in vivo, intravascular measurements of blood constituents, such as pH, oxygen and carbon dioxide. Fluorescence dye indicators whose fluorescence emissions are affected by the blood constituent can be incorporated in a semipermeable polymeric matrix to be attached to an optical fiber to provide highly sensitive sensors. A light source provides a selected wavelength of light which propagates down the optical fiber to excite the dye to fluoresce. The intensity of the fluorescence of the dye is a function of the analyte level in the sample, and can be measured to give an indication of the concentration of the blood constituent.

A fluorescent sensor typically utilizes light in one wavelength region to excite the fluorescent indicator dye to emit light of a different wavelength. A pH sensor may utilize a single dye that exists in acid and base forms, each having a different excitation wavelength. The concentration of carbon dioxide in a sample can similarly be based upon measurement of the pH of a solution of bicarbonate in equilibrium with carbon dioxide from the sample. The bicarbonate and carbon dioxide form a pH buffer system in which the hydrogen ion concentration generally varies with the carbon dioxide concentration. In this manner, the pH or carbon dioxide content of a solution may be measured with dyes such as fluorescein or 8-hydroxy-1, 3, 6 pyrenetrisulfonic acid (HPTS).

Blood oxygen content can similarly be measured with fluorescence quenching techniques which utilize an oxygen-quenchable fluorescent dye that is incorporated in a gas permeable matrix. The intensity of the fluorescence of the dye is a function of the oxygen level in the sample, and can thus be used to measure blood oxygen partial pressure.

In order to be useful for intravascular measurements of blood constituents, such sensors are typically quite small. Such optical fiber microsensors are typically manufactured individually, and are generally complex and difficult to manufacture. Moreover, the prepolymers used for preparation of the dye polymer matrix of the sensors typically polymerize quite rapidly when mixed, so that only small batches can be usefully prepared at a time for construction of a limited number of sensors. An indicator dye is commonly incorporated in a liquid polymeric matrix and the liquid matrix material is converted to a solid matrix in situ on the optical fiber. In one suggested method a vinyl-functional base polymer and crosslinking mixture are deposited in a capillary tube extension at the tip of an optical fiber. A photosensitive initiator causes the mixture to crosslink upon exposure to actinic radiation, to initiate formation of a gel. Unfortunately, the dye, which can be quite toxic, is retained in the gel matrix only by electrostatic forces. This allows the dye to leach out of the sensor, which can produce toxic reactions in the blood stream, and leads to depletion of the dye, with consequent depletion of the intensity of the fluorescence signal.

In another method for fabricating a $CO_2$ microsensor, an aqueous dye-buffer solution and a hydrophobic polymeric precursor with a crosslinking agent and a catalyst are emulsified and allowed to cure. However, the rate of crosslinking is quite rapid, particularly in the presence of the catalyst, and no allowance is made for controlling the rate of cure. This normally results in a short period of working potlife for the liquid matrix material, and represents a barrier to automation of the fabrication process.

In another method of fabricating a pH microsensor, a derivative of cellulose to which a pH sensitive dye is attached is dissolved in hydroxide salts of heavy metals in a diamine or ammonia solution, and regenerated in situ on the optical fiber tip, upon exposure to a dilute acid. The dye matrix is then coated with a mixture of cellulose acetate and carbon black for optical isolation of the sensor. However, the heavy metal elements of the solvent system are incompletely removed, and may leach from the microsensor in blood.

It would therefore be desirable to provide for an improved method for controlling the rate of crosslinking of prepolymers used in forming a stable sensing matrix for such optical fiber sensors, so that the sensing matrix material can be stored for long periods of time in an uncured state and cured on demand to facilitate automation of the manufacturing process.

SUMMARY OF THE INVENTION

Briefly and in general terms, the present invention provides for crosslinking inhibitor compositions for use in an improved method for making an optical fiber microsensor which includes an analyte sensing matrix which is crosslinked in situ over the tip of the optical fiber to yield an ion permeable microsensor which can be used intravascularly to monitor one or more blood parameters. The sensing matrix is preferably prepared in an uncured, liquid form containing a crosslinking inhibitor which can be removed by exposure to elevated temperatures to allow the sensing matrix to crosslink and cure as desired, in situ, on the surface of the optical fiber. Thus, the crosslinking behavior can be closely controlled, significantly facilitating the automation of the fabrication of the optical fiber microsensor.

A liquid crosslinking overcoat layer also containing a crosslinking inhibitor which can be removed by exposure to heat can also be applied in a similar manner over the cured sensing matrix on the optical fiber to facilitate automation of the complete fabrication process. The use of a crosslinking inhibitor thus significantly increases the ease of manufacturing an optical fiber microsensor by prolonging pot life of the analyte sensing matrix and overcoat layers, and allowing for on demand heat curing of each layer.

A primer compound may also be advantageously applied to a portion of the surface of the optical fiber prior to application of the sensing matrix to provide sites for covalent bonding of the sensing matrix to the surface of the optical fiber, to provide improved mechanical strength of the bonding between the matrix and the bonding surface of the optical fiber.

These and other aspects and advantages of the invention will become apparent from the following detailed description.

DETAILED DESCRIPTION OF THE PREFERRED EMBODIMENTS

Polymers utilized in preparation of an analyte sensing matrix of optical fiber sensors typically polymerize quite rapidly. This has heretofore presented an obstacle to automated manufacture of large numbers of optical fiber sensors at a time. The invention advantageously provides for crosslinking inhibitor compositions and a method for controlling the rate of polymerization of prepolymers used in forming a sensing matrix for such optical fiber sensors, so that the dye polymer can be stored in an uncured state and cured on demand in situ on the optical fiber. The invention imparts long potlife to the uncured sensing matrix prepolymer and overcoat mixtures, and allows rapid thermal cure of the sensing matrix and overcoat layers in situ.

According to a first embodiment of the present invention, in fabrication of an optical fiber pH microsensor, the dye indicator material destined for the sensing matrix is covalently bonded to a copolymer to form a dye copolymer. The dye copolymer is then mixed with a blocked crosslinking agent, which can thereafter be crosslinked and covalently bonded to the tip of the optical fiber as desired by heat curing. A polymeric sensing matrix for the pH microsensor is preferably formed from a mixture of a dye bearing copolymer and a blocked form of a crosslinking agent which is a polyether polyisocyanate such as that sold under the trademark "HYPOL" and made by W. R. Grace & Co., with an isocyanate blocking agent added.

The dye bearing copolymer is preferably formed from approximately 95% hydroxyethyl methacrylate (HEMA) and approximately 5% N-(3-aminopropyl) methacrylate hydrochloride (APMA) which yields a poly(2-ethylmethacrylate)-co-N-(3-aminopropyl) methacrylamide hydrochloride (HEMA/APMA) copolymer. The polymerization preferably takes place in n-propanol, and is typically followed by reaction with potassium methoxide to convert ammonium ions to free amines. The copolymer is then typically purified and added to sufficient dimethylformamide (DMF) to provide a polymer concentration of approximately 1.8% by weight. The dye indicator substance is then preferably covalently bonded to the copolymer. The sulfonyl chloride derivatized form of acetoxy-protected HPTS, (Ac-HPTS)-(SO$_2$Cl)$_x$ is then preferably covalently bonded to the copolymer under basic conditions by addition of approximately 10 meq. triethylamine per gram of polymer, and approximately 0.05 meq. Na$_2$CO$_3$ per gram of polymer.

The general equilibrium for preparation of the blocked crosslinking agent described above is shown in Equation 1.

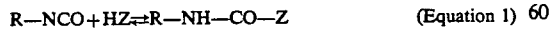
(Equation 1)

where HZ is the blocking agent, and R represents the general dye polyether polyisocyanate copolymer. Blocking agents which can be used include but are not limited to ethanol, o-nitrophenol, resorcinol, benzenethiol, acetyl acetone, 2-methyl-2-propanol, p-chlorophenol, phloroglucinol, ethyl acetoacetate, acetone oxime, methyl ethyl ketone oxime, n-cresol, guaiacol, 1-dodecanthiol, diethyl malonate, diphenyl amine, phenol caprolactam, 2,4-diisobutylphenol, monomethylaniline, and isooctylphenol. The blocked prepolymer mixture containing the pH sensitive dye copolymer can be stored until ready for application to a prepared optical fiber, such as by automated dipping of a number of optical fibers in the mixture.

In one preferred example of formation of the blocked form of the crosslinking agent, a slight stoichiometric excess of acetone oxime, approximately 1.05 equivalents per equivalent isocyanate groups, is added to polyether isocyanate (HYPOL). This mixture is allowed to react at slightly elevated temperatures, at about 40° C., for from about 2 to 24 hours, in a solution of dry acetone to give a blocked polyether isocyanate solids concentration of approximately 37% by weight.

The blocked isocyanate prepolymer is then preferably added to a 10% by weight concentration of the dye-bearing copolymer in DMF to give about a 6:1 weight ratio between the blocked isocyanate prepolymer and the dye copolymer.

The mixture can then be cured to form the dye polymer matrix by exposing the dipped optical fibers to high heat, preferably from about 140° to about 180° C., to cause thermal dissociation or decomposition of the blocking agent, as shown in Equation 2.

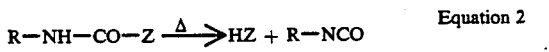
Equation 2

Reaction with water forms an unstable carbamic acid which can decompose to form an amine which will react with the isocyanate crosslinking agent to form a substituted carbonate which can decompose, to form the crosslinked polyether polyisocyanate, as shown in Equations 3-5.

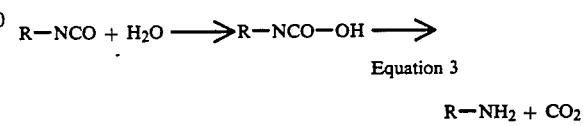
Equation 3

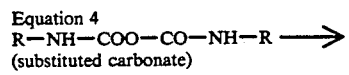
Equation 4
(substituted carbonate)

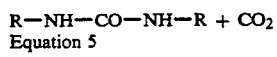
Equation 5

A coating of reflective material is also preferably provided over the cured dye matrix, to retain and reflect both the irradiating light and the fluorescence emissions from the dye indicator within the microsensor. The reflective coating is preferably formed from a suspension of titanium dioxide pigment in water, with the pigment preferably comprising approximately ⅔ of the dispersion by weight, and a blocked form of polyether polyisocyanate prepared as outlined above. The overcoat is applied to the optical fiber by dipping the optical fiber in the uncured liquid overcoat mixture, and applying high heat, such as from about 140° to about 180° C., to cause thermal dissociation of the blocking agent and initiate curing of the overcoat.

In a second embodiment of the invention, an optical fiber microsensor suitable for measuring the partial pressure of $CO_2$ in blood intravascularly can similarly be prepared with a sensing matrix that comprises a pH sensitive dye such as fluorescein or HPTS, which can be bonded to acrylamide or 2-hydroxyethyl methacrylate (HEMA) for example, and a bicarbonate buffer in an aqueous phase. The aqueous phase preferably forms from about 9% to 17% by weight of an emulsion with an uncured vinyl terminated dimethyldiphenylsiloxane copolymer. An emulsion stabilizer may also comprise from 10 to 30% by weight of the aqueous phase. The aqueous phase and the uncured siloxane copolymer are vigorously mixed together in liquid form, so that aqueous phase will be homogeneously dispersed throughout the siloxane copolymer. The siloxane copolymer also preferably includes a crosslinking catalyst, such as platinum, which is believed to facilitate the reaction of the methylhydro and vinyl portions of the siloxane copolymer to form crosslinks. The siloxane copolymer also preferably contains a curing inhibitor to prevent the siloxane copolymer from crosslinking and to allow the matrix to remain liquid for application to an optical fiber. A preferred crosslinking blocker for siloxane copolymer is a vinyl terminated dimethylsiloxane, 1, 3-divinyl tetramethyldisiloxane, having the following chemical structure.

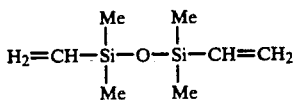

This inhibitor is available from Huls America Inc. under the name D6210, and is believed to act as an inhibitor by more readily competing for sites on the catalyst surface so that they are no longer available to the vinyl and methylhydro functionalities which are believed to crosslink the vinyl terminated dimethyldiphenylsiloxane.

The optical fiber is preferably dipped in the uncured matrix material containing the aqueous sensing solution. The matrix material on the optical fiber is then preferably heated to an elevated temperature above the boiling point of the inhibitor, and preferably to approximately 175° C. in the case of 1, 3-divinyl tetramethyldisiloxane which has a boiling point of 135° C., to cause the crosslinking inhibitor to be dissipated from the matrix material. The matrix material thus is allowed to cure in situ on the optical fiber to form the microsensor, while the aqueous sensing solution remains suspended in liquid form within the matrix.

A coating of reflective material is preferably provided over the cured dye material, to retain the irradiating light and the fluorescence emissions from the dye indicator within the microsensor. The reflective coating in this second embodiment is preferably formed from a dispersion of titanium dioxide pigment in a vinyl terminated prepolymer which preferably reacts with a methylhydrodimethylsiloxane cross-linking agent upon addition of a catalyst such as platinum and moderated by an inhibitor such as 1, 3-divinyl tetramethyldisiloxane at approximately 40 ppt. The overcoat is applied to the optical fiber by dipping the optical fiber in the uncured liquid overcoat mixture, and applying high heat, such as approximately 175° C., to exceed the boiling point of the inhibitor to dissipate the blocking agent and initiate curing of the overcoat.

In a third preferred embodiment of the invention, an optical fiber microsensor for measuring blood oxygen partial pressure of oxygen intravascularly can be prepared with a dye copolymer matrix that comprises an organosiloxane copolymer such as a methylhydrodimethylsiloxane copolymer, to which polynuclear aromatic dye materials, such as coronene and decacyclene for example, have been covalently linked, as by binding to a vinyl functional aliphatic linker moiety which is hydrosilylated to the organosiloxane copolymer. In this form, the polynuclear aromatic dye materials bound to the organosiloxane copolymer are mixed in a ratio of 3 parts coronene to 1 part decacyclene, for example. A crosslinking catalyst such as platinum is preferably used in the step of hydrosilating the dye to the organosiloxane prepolymer, and is preferably also present in the prepolymer mixture to catalyse hydrosilation of the dye copolymer to the vinyl functional polydimethylsiloxane. A crosslinking inhibitor such as the divinyl terminated dimethylsiloxane inhibitor, 1, 3-divinyl tetramethyldisiloxane, described above, is also added to the prepolymer mixture to prevent premature crosslinking of the dye copolymer with the vinyl functional prepolymer. The inhibitor is preferably introduced in the prepolymer mixture in a sufficient amount to reach a final concentration in the mixture of approximately 4.4 parts per thousand.

The optical fiber is preferably dipped in the uncured matrix material containing the oxygen sensitive dye material. The uncured matrix on the optical fiber is then preferably heated to an elevated temperature above the boiling point of the inhibitor, preferably to approximately 200° C. for from 10 to 30 seconds. in the case of 1, 3-divinyl tetramethyldisiloxane, to eliminate the crosslinking inhibitor from the matrix material. The matrix material can then proceed to cure in situ on the optical fiber to form the oxygen sensing microsensor.

A coating of reflective material is preferably provided over the cured oxygen sensing matrix, to reflect irradiating light and fluorescence emissions from the dye indicator within the microsensor. The reflective coating is again preferably formed from a dispersion of titanium dioxide pigment in a vinyl terminated prepolymer which preferably comprises a methylhydrodimethylsiloxane crosslinking agent containing a catalyst such as platinum and a concentration of approximately 40 ppt of a crosslinking inhibitor such as 1, 3-divinyl tetramethyldisiloxane. The overcoat is applied to the optical fiber by dipping the optical fiber in the uncured liquid overcoat mixture, and exposing the optical fiber to an elevated temperature, such as approximately 220° C., sufficient to exceed the boiling point of the inhibitor to remove the blocking agent so that crosslinking of the overcoat material occurs.

According to the method of the invention, and utilizing the sensing matrix compositions described above, an optical fiber microsensor can be manufactured in the following steps. An optical fiber is first dipped in sulfuric acid for approximately 5 seconds, rinsed in water for approximately 10 seconds, and dried in an oven for approximately 5 seconds to clean and prepare the surface of the tip of the optical fiber. The tip of the optical fiber is next dipped in a primer for improving bonding of the matrix material to the optical fiber, such as a silanizing agent, which is preferably isocyanatopropyltriethoxysilane for preparation of a pH sensitive microsensor, and vinyltriethoxysilane for preparation of oxygen or carbon dioxide microsensors. The optical fiber tip is then rinsed in a silanizing agent solvent, which is preferably hexane for preparation of the pH sensitive microsensor, and isopropanol for oxygen and carbon dioxide microsensors. The silanizing agent solvent is preferably removed by drying in an oven for about 5 seconds, and the optical fiber tip is dipped in the appropriate liquid matrix material described above, which adheres to the prepared surface of the optical fiber, for preparation of a pH, oxygen or carbon dioxide sensor. The matrix material on the optical fiber is then preferably cured by exposure of the optical fiber tip to an elevated temperature of from about 140° to about 240° C., for approximately 10–60 seconds, and preferably about 175° C. for approximately 20 seconds, or about 220° for approximately 15 seconds. Thereafter, the sensing matrix portion of the optical fiber tip is preferably dipped in the appropriate liquid overcoat material for preparation of the pH, oxygen or carbon dioxide sensors, and the liquid overcoat adhering over the sensing matrix is then cured by exposure in an oven to an elevated temperature of from about 140° to about 220° C. for from about 10–60 seconds, and preferably about 175° C. for approximately 30 seconds, completing the fabrication of the microsensor.

From the foregoing it will be appreciated that the crosslinking inhibitor compositions and method for controlling the crosslinking of prepolymers used in forming an optical fiber microsensor facilitate the automation of the fabrication of such a microsensor by prolonging the working life of the liquid sensing matrix material and the liquid overcoat material that are applied to the optical fiber. The crosslinking of the sensing matrix and overcoat layer in situ on the surface of the optical fiber can advantageously also be initiated by exposure to elevated temperatures.

While particular forms of invention have been described, it will be apparent that various modifications can be made without departing from the spirit and scope of this invention. Accordingly, it is not intended that the invention be limited, except as by the appended claims.

What is claimed is:

1. A method of making an analyte sensor including an optical fiber having a surface portion covered with a polymeric analyte sensing matrix including a dye indicator material, comprising the steps of:
   preparing an analyte permeable polymer with an analyte sensitive indicator dye covalently bonded to the analyte permeable polymer to form a liquid polymeric analyte sensing matrix;
   forming a liquid mixture of said liquid polymeric analyte sensing matrix with a crosslinking agent and a crosslinking inhibitor which can be removed by exposure to heat;
   coating said optical fiber surface portion with said liquid mixture; and
   heating said liquid mixture on said optical fiber surface portion for a sufficient period of time to remove said crosslinking inhibitor from said liquid mixture, whereby said crosslinking agent crosslinks said liquid polymeric analyte sensing matrix in situ on said optical fiber surface portion thereby producing a cured sensing matrix.

2. The method of claim 1, wherein said crosslinking agent comprises a blocked polyether isocyanate incorporating said crosslinking inhibitor selected from the group consisting of ethanol, o-nitrophenol, resorcinol, benzenethiol, acetyl acetone, 2-methyl-2-propanol, p-chlorophenol, phloroglucinol, ethyl acetoacetate, acetone oxime, methyl ethyl ketone oxime, m-cresol, guaiacol, 1-dodecanthiol, diethyl malonate, diphenyl amine, phenol caprolactam, 2, 4-diisobutylphenol, monomethylaniline, and isoocytylphenol.

3. The method of claim 2, wherein said crosslinking inhibitor is acetone oxime.

4. The method of claim 2, wherein said liquid polymeric analyte sensing matrix comprises a copolymer of hydroxyethyl methacrylate and N-(3-aminopropyl) methacrylate hydrochloride.

5. The method of claim 4, wherein said dye indicator material comprises 8-hydroxy-1, 3, 6 pyrenetrisulfonic acid.

6. The method of claim 1, wherein said liquid polymeric analyte sensing matrix comprises a crosslinkable vinyl terminated organosiloxane, said crosslinking agent comprises a catalyst and said crosslinking inhibitor comprises a vinyl terminated dimethylsiloxane.

7. The method of claim 6, wherein said crosslinking inhibitor has the chemical structure

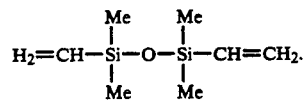

8. The method of claim 6, wherein said crosslinking inhibitor is divinyl tetramethyldisiloxane.

9. The method of claim 6, wherein said dye indicator material is selected from the group consisting of fluorescein and 8-hydroxy-1, 3, 6 pyrenetrisulfonic acid.

10. The method of claim 9, wherein said dye indicator material is covalently bonded with a copolymer selected from the group consisting of acrylamide, hydroxyethyl methacrylate, and a copolymer of hydroxyethyl methacrylate and N-(3-aminopropyl) methacrylate hydrochloride.

11. The method of claim 6, wherein said dye indicator material is selected from the group consisting of coronene and decacyclene, and a combination thereof.

12. The method of claim 9, wherein said liquid polymeric analyte sensing matrix comprises methylhydrodimethylsiloxane copolymer.

13. The method of claim 6, wherein said dye indicator material comprises a polynuclear aromatic dye covalently linked to the organosiloxane copolymer.

14. The method of claim 1, wherein said liquid mixture on said optical fiber surface portion is heated to a temperature exceeding the boiling point or temperature of decomposition of said crosslinking inhibitor.

15. The method of claim 1, wherein said liquid mixture on said optical fiber surface portion is exposed to a temperature of from about 140° to about 240° C. for approximately 10–60 seconds.

16. The method of claim 1, wherein said liquid mixture on said optical fiber surface portion is exposed to a temperature of about 220° C. for approximately 15 seconds.

17. The method of claim 1, wherein said liquid mixture on said optical fiber surface portion is exposed to a temperature of about 175° for approximately 20 seconds.

18. The method of claim 1, further including the step of applying a layer of an uncured overcoat mixture comprising a second crosslinking agent and a second crosslinking inhibitor which can be removed by exposure to elevated temperature over said liquid polymeric analyte sensing matrix following said step of heating said liquid mixture; and heating said uncured overcoat mixture on said optical fiber surface portion for a sufficient period of time to remove said second crosslinking inhibitor from said uncured overcoat mixture, whereby said second crosslinking agent crosslinks said overcoat mixture in situ over said cured sensing matrix.

19. The method of claim 18, wherein said overcoat mixture includes titanium dioxide.

20. The method of claim 18, wherein said overcoat second crosslinking agent comprises a blocked form of a polyether isocyanate incorporating said second crosslinking inhibitor, and said second crosslinking inhibitor is selected from the group consisting of ethanol, o-nitrophenol, resorcinol, benzenethiol, acetyl acetone, 2-methyl-2-propanol, p-chlorophenol, phloroglucinol, ethyl acetoacetate, acetone oxime, m-cresol, guaiacol, 1-dodecanthiol, diethyl malonate, diphenyl amine, phenol caprolactam, 2,4-diisobutylphenol, monomethylaniline, and isooctylphenol.

21. The method of claim 18, wherein said overcoat second crosslinking inhibitor comprises acetone oxime.

22. The method of claim 18, wherein said overcoat second crosslinking agent comprises a crosslinkable vinyl terminated organosiloxane and a catalyst, and said second crosslinking inhibitor comprises a vinyl terminated dimethylsiloxane.

23. The method of claim 22, wherein said second crosslinking inhibitor has the chemical structure

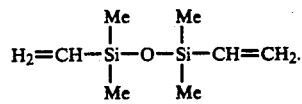

24. The method of claim 22, wherein said second crosslinking inhibitor is divinyl tetramethyldisiloxane.

25. The method of claim 22, wherein said overcoat mixture comprises methylhydrodimethylsiloxane copolymer.

26. The method of claim 18, wherein said uncured overcoat mixture on said cured sensing matrix is heated to a temperature exceeding the boiling point or temperature of decomposition of said second crosslinking inhibitor.

27. The method of claim 18, wherein said uncured overcoat mixture on said cured sensing matrix is exposed to a temperature of from about 140° to about 220° C.

28. The method of claim 18, wherein said uncured overcoat mixture on said cured sensing matrix is exposed to a temperature of from about 140° to about 220° C. for approximately 10 to 60 seconds.

29. The method of claim 18, wherein said uncured overcoat mixture on said cured sensing matrix is exposed to a temperature of about 175° for approximately 30 seconds.

30. The method of claim 1, further including the step of priming said optical fiber surface portion by applying a silanizing agent selected from the group consisting of isocyanatopropyltriethoxysilane and vinyltriethoxysilane to said optical fiber surface portion prior to said step of coating said optical fiber surface portion with said liquid mixture.

* * * * *

UNITED STATES PATENT AND TRADEMARK OFFICE
CERTIFICATE OF CORRECTION

PATENT NO.   : 5,326,585
DATED        : July 5, 1994
INVENTOR(S)  : Alan M. Nelson; Carmen L. Soikowski It is certified that error appears in the above-indentified patent and that said Letters Patent is hereby corrected as shown below:

In Column 3, line 68, delete "n-cresol" and insert --m-cresol--.

Signed and Sealed this

Third Day of January, 1995

Attest:

BRUCE LEHMAN

*Attesting Officer*  *Commissioner of Patents and Trademarks*